Figure 1:
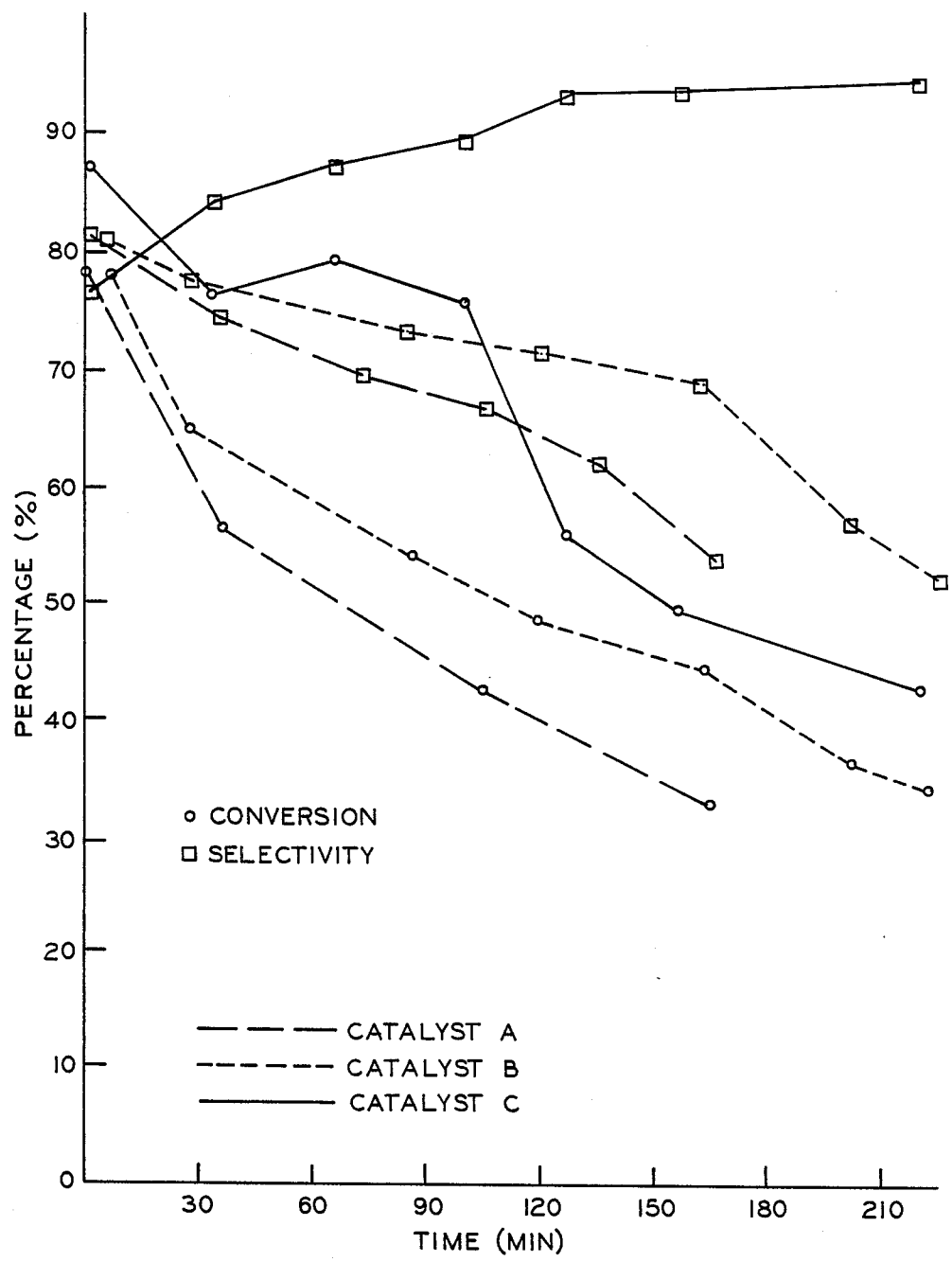

__United States Patent__ [19]

Eastman et al.

[11] Patent Number: 4,835,127

[45] Date of Patent: May 30, 1989

[54] OXIDATIVE DEHYDROGENATION AND CRACKING OF PARAFFINS USING A PROMOTED COBALT CATALYST

[75] Inventors: Alan D. Eastman; Jack P. Guillory; Charles F. Cook; James B. Kimble, all of Bartlesville, Okla.

[73] Assignee: Phillips Petroleum Company, Bartlesville, Okla.

[21] Appl. No.: 658,978

[22] Filed: Oct. 9, 1984

Related U.S. Application Data

[62] Division of Ser. No. 552,557, Nov. 16, 1983, Pat. No. 4,497,971.

[51] Int. Cl.$^4$ .................. B01J 27/185; B01J 27/14; B01J 27/043; B01J 27/128

[52] U.S. Cl. .................. 502/213; 502/208; 502/222; 502/229

[58] Field of Search .............. 502/208, 213, 222, 229

[56] References Cited

U.S. PATENT DOCUMENTS

| | | | |
|---|---|---|---|
| 3,248,432 | 4/1966 | Riley et al. | 502/208 X |
| 3,781,223 | 12/1973 | Walker | 502/213 |
| 3,784,483 | 1/1974 | Cichowski | 502/213 |
| 3,789,017 | 1/1974 | Walker | 502/213 |
| 3,790,501 | 2/1974 | Walker | 502/213 |
| 3,792,103 | 2/1974 | Walker | 585/658 X |
| 3,810,953 | 5/1974 | Cichowski | 585/658 X |
| 3,845,156 | 10/1974 | Farha, Jr. | 502/213 X |
| 3,852,369 | 12/1974 | Walker et al. | 585/658 X |
| 3,926,845 | 12/1975 | Cichowski | 502/213 X |
| 4,048,246 | 9/1977 | Antos | 585/661 X |
| 4,252,680 | 2/1981 | Walker et al. | 502/208 |
| 4,368,344 | 1/1983 | Kolts | 585/661 X |
| 4,368,346 | 1/1983 | Eastman | 585/658 |
| 4,396,537 | 8/1983 | Eastman | 502/213 |
| 4,410,752 | 10/1983 | Blum et al. | 585/658 |

FOREIGN PATENT DOCUMENTS 2050188A 2/1980 United Kingdom ............... 502/213

*Primary Examiner*—William G. Wright
*Attorney, Agent, or Firm*—J. Michael Simpson

[57] ABSTRACT

A paraffin or mixture of paraffins having from 2 to 5 carbon atoms is oxidatively dehydrogenated in the presence of a cobalt based catalyst composition which has been calcined in the absence of oxygen. The catalyst composition comprises cobalt; phosphorus; at least one promoter selected from the group consisting of zinc, titanium, zirconium, niobium, indium, lead and bismuth; at least one alkali metal and oxygen. The catalyst composition may also contain sulfur and/or a halogen. If the feed to the oxidative dehydrogenation process contains paraffins having more than two carbon atoms, some cracking of such paraffins will also occur at the conditions at which the oxidative dehydrogenation process is carried out.

12 Claims, 1 Drawing Sheet

OXIDATIVE DEHYDROGENATION AND CRACKING OF PARAFFINS USING A PROMOTED COBALT CATALYST

This application is a division of application Ser. No. 552,557, filed Nov. 16, 1983, now U.S. Pat. No. 4,497,971.

This invention relates to an improved catalytic process for the cracking and oxidative dehydrogenation of light paraffins, and a catalyst therefor.

Oxidative dehydrogenation processes for the conversion of paraffins to olefins are well known. Cobalt based catalysts are commonly used as the oxidative dehydrogenation catalyst. However, improving the selectivity and conversion of any catalyst composition is desirable and it is an object of this invention to provide a cobalt based catalyst composition which has an improved selectivity and conversion for the oxidative dehydrogenation of light paraffins and thus provides an improved process for the oxidative dehydrogenation of light paraffins.

A common oxidative dehydrogenation reaction is the conversion of ethane to ethylene. However, in some cases it would be desirable to convert a paraffin having more than two carbon atoms to ethylene. It is thus a further object of this invention to provide a cobalt based catalyst composition which not only has oxidation dehydrogenation capabilities but also has the capability to crack paraffins having more than two carbon atoms so that a paraffin such as propane can be converted to ethylene.

In accordance with the present invention, a paraffin or mixtures of paraffins having from 2 to 5 carbon atoms is oxidatively dehydrogenated in the presence of a cobalt based catalyst composition which has been calcined in the absence of oxygen. The catalyst composition comprises cobalt; phosphorus; at least one promoter selected from the group consisting of zinc, titanium, zirconium, niobium, indium, lead and bismuth; at least one alkali metal and oxygen. Sulfur may be added to the catalyst composition to improve the selectivity and conversion of the catalyst composition.

The conversion of the oxidative dehydrogenation process may also be improved by introducing a halogen at least periodically into the process. The improved conversion may also be obtained initially by using a compound containing a halogen to prepare the catalyst composition. If a halogen is introduced into the process, the catalyst composition will contain such halogen and will retain the halogen for a period of time after introduction of the halogen is terminated.

If the feed to the oxidative dehydrogenation process contains paraffins having more than two carbon atoms, some cracking of such paraffins will occur at the conditions at which the oxidative dehydrogenation process is carried out.

Calcination in the absence of free oxygen is a particularly advantageous feature of the present invention. Conventional calcination procedures generally require the presence of oxygen. However, it is believed that, in the case of the present catalyst composition, calcination in the absence of oxygen results in a catalyst which is in an oxide form but is not in the higher oxide form which would result from calcination in the presence of oxygen. Maintaining the catalyst composition in the lower oxide form is believed to result in a more active catalyst.

In the process of the present invention, it is believed that the oxygen required for the oxidative dehydrogenation of the paraffin is supplied from the catalyst composition. Thus, the oxidative dehydrogenation can be carried out in a cyclic manner in which the catalyst composition is contacted alternately with a feed stream containing a light paraffin and a gaseous stream containing free oxygen. However, the oxidative dehydrogenation can also be effected continuously by passing a feed stream containing a light paraffin plus free oxygen in contact with the catalyst composition under suitable oxidative dehydrogenation conditions.

If the catalyst composition is prepared using a compound containing a halogen, at least a part of the halogen will remain in the catalyst composition unless specific steps are taken to completely remove the halogen. The halogen remaining in the catalyst composition will improve the conversion of the process for a period of time (on the order of 15-25 cycles) but the beneficial effects of the halogen are soon lost because the halogen is removed as a volatile compound from the catalyst and does not remain in the process. The benefits of the halogen may be maintained by at least periodically introducing a halogen into the process. Such introduction insures the presence of a halogen in the catalyst composition and thus in the process and the benefits of the halogen are retained over a long period of time. Even if the introduction of the halogen is terminated for a period of time, the halogen being volatilized from the catalyst composition will continue to provide a beneficial effect for a period of time and thus a periodic introduction of the halogen may be used.

Other objects and advantages of the invention will be apparent from the foregoing brief description of the invention and the appended claims as well as from the detailed description of the invention which follows.

The drawing, which is utilized to present data from Example 1, is briefly described as follows:

FIG. 1 is a graphical presentation of data from Example 1 which demonstrates the benefits of the present invention.

Paraffins which can be oxidatively dehydrogenated in accordance with the present invention are paraffins which have from 2 to 5 carbon atoms per molecule. The oxidative dehydrogenation process of the present invention is particularly applicable to the conversion of ethane to ethylene.

Paraffins which can be cracked in accordance with the present invention are paraffins which have from 3 to 5 carbon atoms per molecule. Again, the cracking aspect of the present invention is particularly advantageous from the standpoint of converting paraffins such as propane and butane to ethylene in combination with the oxidative dehydrogenation process.

The catalyst composition employed in the process of the present invention comprises cobalt; phosphorus; at least one promoter selected from the group consisting of zinc, titanium, zirconium, niobium, indium, lead and bismuth; at least one alkali metal and oxygen. Zirconium is the preferred promoter. The catalyst composition may also contain sulfur and/or at least one halogen. Sufficient oxygen is present in the catalyst composition to satisfy the valence requirements of the cobalt, phosphorus, the at least one promoter and the at least one alkali metal. If the halogen is present, the halogen will replace some oxygen.

The at least one alkali metal is selected from the group consisting of lithium, sodium, potassium, rubidium and cesium. The preferred alkali metals are sodium and potassium.

The halogens which may be used in the process of the present invention comprise chlorine, bromine and iodine. The presently preferred halogen is chlorine.

The catalyst composition can be prepared by any suitable method. Preferably, soluble salts of cobalt (preferably cobalt sulfide if sulfur is to be added) and the promoter are combined in solution and coprecipitated with a suitable base to form a mixture of hydroxides, hydrous oxides, carbonates, sulfonates or other insoluble forms. The coprecipitate is then separated from the solution and phosphorus and at least one alkali metal are added in the quantity required. The phosphorus and alkali metal can be added as dry, powdered solids, as solutions of separate compounds or as a single compound, i.e., sodium phosphate or potassium phosphate.

If it is desired to initially incorporate a halogen into the catalyst composition, such halogens may be added by using a halogen containing salt of a compound used to prepare the catalyst. A halogen can also be added in the form of an ammonium halide.

After all of the desired components have been added to the catalyst composition, the catalyst composition is preferably dried and then calcined. The drying step is optional but is particularly desirable where sulfur is present in the catalyst composition and also the calcining step is important with any of the catalysts of the present invention in preparing a particularly active catalyst.

The catalyst composition is preferably dried in the presence of free oxygen (generally air). Any suitable drying temperature may be utilized. The catalyst composition is preferably dried at a temperature in the range of about 100° C. to about 180° C. and more preferably in the range of about 130° C. to about 150° C. Any suitable drying time may be utilized for the catalyst composition. The drying time will generally be at least about 5 hours and the catalyst composition may be dried overnight or for longer times if desired. Again, it is believed that the drying step is particularly desirable where sulfur is present in the catalyst to remove at least a portion of the sulfur. Also, components of the catalyst are converted to an oxide form during the drying step.

The catalyst composition is calcined in the absence of free oxygen. Preferably, the catalyst composition is calcined in an inert atmosphere such as nitrogen or helium. It is also believed that the catalyst composition could be calcined in the presence of a reducing gas such as hydrogen. The catalyst composition could also be calcined in a vacuum but this would generally not be commercially feasible.

The catalyst composition may be calcined at any suitable temperature. Generally, the calcining temperature will be in the range of about 450° C. to about 850° C. and more preferably in the range of about 700° C. to about 800° C. The catalyst composition may be calcined for any suitable time. The calcining time will generally be in the range of about 1 to about 12 hours and more preferably in the range of about 2 to about 5 hours.

It is believed that the above stated drying and calcining procedure results in a more active and selective cobalt based catalyst because the cobalt is not converted as completely to the $Co_3O_4$ state as would occur if the catalyst composition were calcined in the presence of oxygen. Rather, more of the cobalt remains in the CoO state which is believed to be more catalytically active and selective for the oxidative dehydrogenation and cracking of paraffins in accordance with the present invention.

In observing the finished catalyst composition, it has been found that a brown color generally indicates a good catalyst while a black color generally indicates a catalyst with poor performance characteristics. Since CoO is lighter than $Co_3O_4$, it is believed the brown color indicates a higher concentration of CoO which is again believed to be one of the basic differences in the catalyst composition which results in a more active and selective catalyst.

The catalyst composition may also be prepared by mixing the catalyst components as dry powders or as wet paste in the oxide form or as compounds readily convertible to oxides by heating in the presence of oxygen. Water or concentrated aqueous ammonia are preferred wetting agents to form the wet paste. After the catalyst components are intimately mixed, the mixture is preferably dried and then calcined as described above.

If it is desired to incorporate a halogen into the catalyst composition using this second method of preparation, the catalyst composition may be prepared by adding some catalyst components in the halide form. Also, an ammonium halide may be included in the mixture of catalyst components.

Any suitable atomic ratio of cobalt to the metal promoter may be utilized in the catalyst composition. Preferably the atomic ratio of cobalt to the metal promoter is in the range of about 1:1 to about 20:1 and is more preferably in the range of about 3:1 to about 6:1. Any suitable concentration of phosphorus may be utilized in the catalyst composition. Preferably the concentration of phosphorus is in the range of about 1 to about 10 weight percent and is more preferably in the range of about 2 to about 5 weight percent calculated as the oxide and based on the weight of the catalyst composition. Any suitable concentration of the alkali metal may be utilized in the catalyst composition. Preferably the concentration of the alkali metal is in the range of about 1 to about 10 weight percent and more preferably in the range of about 2 to about 5 weight percent calculated as the oxide and based on the weight of the catalyst composition. Any suitable concentration of sulfur, if used, may be utilized in the catalyst composition. Preferably the concentration of sulfur is in the range of about 1 to about 10 weight percent and more preferably in the range of about 2 to about 5 weight percent calculated as the element and based on the weight of the catalyst composition. If it is desired to use a halogen, any suitable concentration of the halogen may be used. Preferably, the concentration of the halogen is in the range of about 1 to about 10 weight percent and more preferably in the range of about 2 to about 5 weight percent calculated as the element and based on the weight of the catalyst composition.

Any suitable cobalt compound may be utilized in the catalyst composition. Suitable cobalt compounds include cobalt acetate, cobalt carbonate, cobalt nitrate, cobalt oxides, and cobalt halides. Cobalt sulfide is preferably used as the cobalt compound if sulfur is to be incorporated into the catalyst composition. Other sulfur containing compounds which may be used include the Zr, Co, Na, K or ammonium salts of sulfur, thiocyanide or thiosulfate.

Any suitable compound of the promoting elements may be utilized in the preparation of the catalyst composition. Suitable zinc compounds include zinc acetate, zinc halides, zinc nitrate, zinc carbonate, and zinc oxide. Suitable titanium compounds include titanium tetrachloride and titanium dioxide. Flame hydrolyzed titanium dioxide is particularly preferred because of its very small particle size. Suitable zirconium compounds which may be utilized in preparing the catalyst composition include zirconium tetrachloride, zirconyl nitrate, zirconyl acetate and zirconium dioxide. Suitable niobium compounds which may be utilized in preparing the catalyst composition include niobium (V) chloride and niobium oxide. Suitable indium compounds which may be utilized in preparing the catalyst composition include indium chloride, indium hydroxide, indium nitrate, indium acetate and indium oxide. Suitable lead compounds which may be utilized in preparing the catalyst composition include lead chloride, lead nitrate, lead acetate, lead carbonate and lead oxides. Suitable bismuth compounds which may be utilized in preparing the catalyst composition include bismuth trichloride, bismuth nitrate, bismuth subnitrate, and bismuth trioxide.

The alkali metal and phosphorus are preferably added to the catalyst composition as a single compound that contains both the alkali metal and the phosphorus. As an example, if sodium is to be utilized as the alkali metal then the compounds which could be utilized to add the sodium and phosphorus include sodium dihydrogen orthophosphate, disodium monohydrogen orthophosphate, trisodium orthophosphate, and sodium pyrophosphate. The alkali metal and the phosphorus can also be incorporated into the catalyst as separate compounds. Again, utilizing sodium as an example, suitable sodium compounds for use in preparation of the catalyst include sodium hydroxide, sodium carbonate, sodium bicarbonate, sodium sesquicarbonate, sodium nitrate, and sodium acetate. Suitable phosphorus compounds which may be utilized in preparing the catalyst composition, if it is desired to add phosphorus separately from the alkali metal, include orthophosphoric acid, ammonium phosphates, and ammonium hydrogen phosphates.

The oxidative dehydrogenation and cracking process of the present invention is preferably carried out by means of any apparatus whereby there is achieved an alternate contact of the catalyst composition with the paraffin to be processed and thereafter the catalyst with free oxygen. The process of the present invention is not limited to this type of apparatus and apparatus can be utilized which provide only a continuous contact of the paraffin and free oxygen with the catalyst composition. If a halogen is used, ceramic lined apparatus is preferably used because of the corrosive nature of halogen.

Suitable conditions are described hereinafter in terms of the oxidative dehydrogenation process. These conditions are also suitable for cracking if paraffins containing more than 2 carbon atoms are contained in the feed.

Any suitable oxidative dehydrogenation temperature can be employed which provides the desired degree of catalytic activity in the dehydrogenation of the light paraffins. The oxidative dehydrogenation temperature will generally be in the range of about 480° C. to about 815° C. For the oxidative dehydrogenation of ethane the more preferred temperature is in the range of about 620° C. to about 705° C. The preferred temperature for each of the paraffins which may be oxidatively dehydrogenated in accordance with the present invention decreases below the preferred temperature for the oxidative dehydrogenation of ethane within the broad range of temperature as the carbon number of the paraffin feed increases.

The catalytic oxidative dehydrogenation process can be carried out at any suitable pressure. Below pressures at which the product begins to polymerize, the oxidative dehydrogenation process is not greatly affected by reaction pressure. The pressure of the oxidative dehydrogenation reaction will generally range from about 10 to about 520 kPa and will more preferably range from about 100 to about 200 kPa.

Any suitable feed rate for the feedstock can be utilized. The feedstock may comprise a fluid stream containing either one of the light paraffins or a mixture of the light paraffins and the feed stream may also contain free oxygen. The reactant feed rate expressed as volumes of gas at standard conditions per volume of catalyst per hour (GHSV) will generally range from about 100 to about 2500 with a feed rate of about 500 GHSV being preferred.

If it is desired to introduce a halogen into the process, the halogen may be introduced in any suitable manner. Preferably, the halogen is mixed with the feed stream flowing to the process. Any suitable concentration of the halogen in the feed stream can be utilized. Also continuous or periodic introduction of the halogen in the feed stream can be used. When the halogen is being introduced into the feed stream, the concentration of the halogen is generally maintained in the range of about 1 part per million to about 10 mole percent. The halogen can be added to the feed stream in any suitable manner. The preferred form of addition is in the form of a gaseous halogen compound such as the methyl halides.

Any suitable oxidative dehydrogenation reaction time for the cyclic process may be utilized in the oxidative dehydrogenation process. The oxidative dehydrogenation reaction time will generally be in the range of from about 1 min. to about 30 min. in a cyclic process where oxygen is not being introduced with the feed. The oxidative dehydrogenation cycle preferably will not reduce the cobalt beyond the oxide CoO. Further reduction produces cobalt metal which is not readily regenerated in the presence of free oxygen and causes an irreversible loss of catalyst activity. Consequently it is preferred to keep the dehydrogenation steps sufficiently short that the catalyst does not experience over reduction.

If oxygen is being introduced with the feed, the oxidative dehydrogenation reaction time will generally be long enough that the process is considered continuous. The oxidative dehydrogenation reaction time will generally be at least 1 hour and may be as long as 100 hours if lower activity of the catalyst can be tolerated towards the end of the run. At the end of the run the catalyst is regenerated so in this sense the process could still be considered cyclic. However, the reaction portion of the cycle is long with respect to typical cyclic processes.

Any suitable amount of oxygen may be introduced with the feed. The amount of oxygen introduced will generally be in the range of about 0.4 to about 0.75 moles of oxygen per mole of feed and will preferably be in the range of about 0.5 to about 0.6 moles of oxygen per mole of feed.

The regeneration of the catalyst may be carried out at the temperature and pressure used in the oxidative dehydrogenation step. The duration of the regeneration step should be sufficient to permit at least the stoichiometric quantity of oxygen required to reoxidize the cobalt to pass over the catalyst. The regeneration time will generally be in the range of about one times the length of the oxidative dehydrogenation step to about ten times the length of the oxidative dehydrogenation step.

The following examples are presented in further illustration of the invention.

EXAMPLE I

Catalyst Preparation

Catalysts A and B were prepared by combining 107 g (0.90 moles) of $CoCO_3$, 15.0 g (0.034 moles) $Na_4P_2O_7 \cdot 10H_2O$, 3.0 g (0.053 moles) KOH, 53.4 g (Ca. 0.22 moles) $ZrO(NO_3)_2 \cdot x\ H_2$, and 10.7 g (0.20 moles) of $NH_4Cl$ in sufficient concentrated aqueous ammonia to make a thick paste. After mixing, the preparation was dried in an oven in air at about 140° C. for about 17 hours and then divided into two portions. Catalyst A was obtained by calcining one portion in air for three hours at 815° C., then six hours at 538° C. Catalyst B was obtained by calcining the other portion in nitrogen with the same time-temperature schedule. Care was taken to insure that no oxygen was present in the calcining step for Catalyst B.

Catalyst C was prepared from the same compounds except that cobalt sulfide, prepared by combining aqueous solutions of 0.90 moles of $CoCl_2 \cdot 6H_2O$ with 1.0 mole $Na_2S \cdot 9H_2O$, then separating the CoS by filtration was used. After drying in an oven in air at about 110° C. for 18 hours the preparation was calcined in nitrogen for three hours at 815° C. Again, care was taken to insure that no oxygen was present during the calcining step. Catalysts A, B and C were crushed and sieved to obtain $-20+40$ mesh fractions for testing. Catalysts A, B and C had the same nomina composition (except for sulfur), calculated based on combined metals to be equivalent to:

CoO: 63.58 wt. %
$ZrO_2$: 25.57 wt. %
$Na_2O$: 3.96 wt. %
$K_2O$: 2.36 wt. %
$P_2O_5$: 4.53 wt. %

Some chlorine (0.4 wt. %) remained in the catalyst composition. However, the remaining chlorine was considered a residual amount. No attempt was made to obtain a significant chlorine concentration in Catalysts A, B and C. Catalyst C contained 3.8 wt. % sulfur.

Experimental Results

Catalysts A, B and C were used in continuous runs for the oxidative dehydrogenation of ethane to ethylene. Two mL portions of catalyst diluted with three mL of quartz chips were placed in a tubular quartz reactor mounted vertically in a furnace maintained at 650° C. A mixture of 25 vol. % ethane and 75 vol. % air passed downflow through the reactor at 2400 GHSV at about 3 psig. Heat of reaction raised the catalyst temperature to about 665° C. Snap samples of reaction product were taken periodically into a gas chromatograph to determine ethylene yield and ethane conversion. Results of all runs are plotted in FIG. 1.

Referring now to FIG. 1, it can be seen that with each catalyst, conversion decreases with time. However, the conversion of Catalyst B was significantly increased with respect to Catalyst A which illustrates the significance of the calcining in the absence of oxygen. Further, the conversion of Catalyst C was significantly greater than either Catalyst A or Catalyst B which indicates the significance of the use of cobalt sulfide to prepare the catalyst composition.

With respect to selectivity, it can be seen that the selectivity of both Catalysts A and B decreased with time while the selectivity of Catalyst C increased with time. Also, the selectivity of Catalyst B was again significantly greater than the selectivity of Catalyst A which again illustrates the significance of the calcining in the absence of oxygen.

EXAMPLE II

Catalyst Preparation

Catalyst D was prepared by mixing 9.0 grams $(ZrO(C_2H_3O_2)_2$ (0.04 moles) with 16.7 g (0.18 moles) of cobaltous hydroxide and 2.1 g (0.04 moles) of ammonium chloride as a slurry in concentrated aqueous ammonium hydroxide and then adding 3.0 g (0.0067 moles) of $Na_4P_2O_7 \cdot 10H_2O$ and 0.6 g (0.011 moles) of KOH dissolved in water. The resulting slurry was dried in an oven at about 125° C. and then calcined in air for 3 hours at 815° C. followed by 8 hours at 538° C. The calculated atomic ratio of Co:Zr:P:Na:K was 9:2:0.7:1.3:0.5.

Experimental Results

Catalyst D was used in a run that demonstrated the effect of adding chlorine to the process. A complete process cycle consisted of ethane flowing at 500 GHSV for two minutes followed by air flowing at 1250 GHSV for six minutes. A continuous flow of nitrogen was not used as in Example I. The entire run was made at 675° C. at atmospheric pressure. Periodically, as shown in Table I, gaseous methyl chloride was added to the process. A GHSV of five was sought for the gaseous methyl chloride. However, actual feed rates for the gaseous methyl chloride of up to GHSV=30 were measured because of difficulties in metering the gaseous methyl chloride at the low flow rate. Yields of ethylene from ethane were measured by GLC analysis of snap samples taken at midpoint of the two-minute process cycle. Results through nearly 400 cycles of operation are presented in Table I. Gaseous methyl chloride was added during three periods of the run. During cycles 26-30, 168-201 and 221 gaseous methyl chloride was added to the ethane. During cycles 350-362 gaseous methyl chloride was added to regeneration air but not to the ethane. During each of these intervals the yield of ethylene increased appreciably and then declined when use of methyl chloride was discontinued. It is noted that the effects of introduction of the gaseous methyl chloride do not disappear instantly but rather decrease slowly as the chloride is removed from the catalyst as a volatile compound when the flow of gaseous methyl chloride is terminated.

TABLE 1

| Cycle | $C_2H_6$ Conv. % | $C_2H_4$ Yield, % | $C_2H_4$ Selectivity, % | Comment on $CH_3Cl$ |
|---|---|---|---|---|
| 1 | 32.0 | 23.8 | 74.5 | off |
| 10 | 29.0 | 24.7 | 85.0 | off |
| 14 | 28.1 | 27.7 | 88.0 | off |
| 25 | 26.5 | 24.2 | 91.4 | off |
| 26 | 31.3 | 27.4 | 87.4 | on |
| 30 | 57.7 | 45.4 | 78.7 | on |
| 32 | 54.5 | 45.2 | 83.0 | off |
| 36 | 49.4 | 42.6 | 86.3 | off |
| 39 | 34.8 | 31.3 | 89.9 | off |
| 47 | 30.8 | 28.2 | 91.5 | off |
| 166 | 22.1 | 20.5 | 92.9 | off |

TABLE 1-continued

| Cycle | C$_2$H$_6$ Conv. % | C$_2$H$_4$ Yield, % | C$_2$H$_4$ Selectivity, % | Comment on CH$_3$Cl |
|---|---|---|---|---|
| 168 | 25.0 | 23.2 | 92.9 | on |
| 171 | 29.3 | 25.3 | 86.3 | on |
| 174 | 33.6 | 28.7 | 85.3 | on |
| 185 | 47.0 | 38.0 | 80.9 | on |
| 201 | 71.2 | 51.4 | 72.4 | on |
| 204 | 60.9 | 45.4 | 74.5 | off |
| 216 | 46.4 | 37.3 | 80.3 | off |
| 221 | 46.4 | 38.4 | 82.8 | on for this cycle |
| 226 | 44.3 | 37.1 | 83.8 | off |
| 339 | 24.8 | 21.8 | 87.9 | off |
| 350 | not available | | | on, w/air for regeneration |
| 356 | 34.1 | 29.6 | 86.9 | on, w/air for regeneration |
| 362 | 38.7 | 33.3 | 86.2 | on, w/air for regeneration |
| 370 | 34.0 | 30.0 | 88.2 | off |
| 378 | 34.6 | 30.3 | 87.7 | off |
| 386 | 36.6 | 32.1 | 87.8 | off |
| 393 | 36.1 | 31.6 | 87.7 | off |

Based on the results set forth in Table I, it is believed that the addition of a halogen would also be beneficial where the catalyst composition has been calcined in the absence of oxygen or contains sulfur.

EXAMPLE III

A second batch of Catalyst C prepared as in Example I was tested for oxidative cracking with propane, butane and isobutane feeds in a continuous run. A 5 mL portion of Catalyst C was placed in a tubular quartz reactor and subjected to the same pressure, flow and temperature conditions as in Example I with a feed of 25 vol. % hydrocarbon and 75 vol. % air at 2400 GHSV.

The gaseous reactor effluent was analyzed by standard gas chromatographic methods. The conversion of each feed and the product distribution are shown on Table II.

Each feed was run for 45 to 60 minutes continuously. For comparison, tests over quartz chips in place of catalyst are included. In all cases, the catalysts show more conversion and more selectivity to desired products, ethylene and propylene, than the quartz chips.

Ethane was used as the initial and final feed to indicate catalyst activity over the extended test. The final run shows lower activity than the fresh catalyst indicating the catalyst deactivates without regeneration.

That which is claimed is:

1. A catalyst composition comprising cobalt; phosphorus; at least one promoter selected from the group consisting of zinc, titanium, zirconium, niobium, indium, lead and bismuth; at least one alkali metal; and oxygen, wherein said catalyst composition is calcined in an inert atmosphere.

2. A composition in accordance with claim 1 wherein said catalyst composition is calcined in a nitrogen atmosphere at a temperature in the range of about 450° C. to about 850° C. for a time in the range of about 1 hour to about 12 hours.

3. A composition in accordance with claim 1 wherein said catalyst composition is calcined in a nitrogen atmosphere at a temperature in the range of about 700° C. to about 800° C. for a time in the range of about 2 hours to about 5 hours.

4. A composition in accordance with claim 1 wherein said at least one promoter is zirconium.

5. A composition in accordance with claim 1 wherein the atomic ratio of cobalt to said at least one promoter is in the range of about 1:1 to about 20:1, wherein the concentration of phosphorus in said catalyst composition is in the range of about 1 to about 10 weight percent calculated as the oxide and based on the weight of said catalyst composition and wherein the concentration of said at least one alkali metal is in the range of about 1 to about 10 weight percent calculated as the oxide and based on the weight of said catalyst composition.

6. A composition in accordance with claim 1 wherein the atomic ratio of cobalt to said at least one promoter is in the range of about 3:1 to about 6:1, wherein the concentration of phosphorus is in the range of about 2 to about 5 weight percent calculated as the oxide and based on the weight of said catalyst composition, and wherein the concentration of said at least one alkali metal is in the range of about 2 to about 5 weight percent calculated as the oxide and based on the weight of said catalyst composition.

7. A composition in accordance with claim 1 wherein said catalyst composition additionally comprises sulfur.

8. A composition in accordance with claim 7 wherein said sulfur is added to said catalyst composition by utilizing cobalt sulfide to prepare said catalyst composition.

9. A composition in accordance with claim 8 wherein said catalyst composition is dried in the presence of free oxygen at a temperature in the range of about 100° C. to

TABLE II

| Feed* | Catalyst | Temp.(°C.) | Hydrocarbon Conv. % | % Selectivity to: | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$H$_8$ + C$_4$H$_6$ | CO$_2$ + CO |
| C$_2$H$_6$ | C | 672 | 68.0 | 0.3 | 84.4 | 0 | 2.9 | 0.3 | 0 | 8.8 |
| C$_2$H$_6$ | C | 686 | 79.0 | 0.4 | 85.8 | 0 | 1.9 | 0.4 | 0.3 | 8.8 |
| C$_2$H$_6$ | C | 670 | 85.0 | 1.5 | 86.4 | 0 | 0.2 | 1.5 | 0 | 9.5 |
| C$_2$H$_6$ | Quartz | 671 | 3.0 | 0 | 91.2 | 0 | 0 | 0 | 0 | 8.8 |
| n-C$_4$H$_{10}$ | C | 665 | 67.6 | 9.7 | 35.8 | 2.9 | 31.7 | 1.6 | 12.4 | 5.9 |
| n-C$_4$H$_{10}$ | C | 668 | 63.7 | 9.5 | 35.5 | 2.3 | 31.7 | 1.6 | 13.8 | 5.9 |
| n-C$_4$H$_{10}$ | Quartz | 669 | 21.2 | 9.2 | 23.9 | 1.2 | 29.2 | 4.6 | 17.5 | 14.5 |
| iso-C$_4$H$_{10}$ | C | 665 | 49.5 | 12.1 | 1.7 | 1.4 | 45.8 | 0 | 32.6 | 6.4 |
| iso-C$_4$H$_{10}$ | C | 671 | 47.8 | 12.0 | 2.1 | 2.2 | 45.2 | 0 | 32.5 | 6.0 |
| iso-C$_4$H$_{10}$ | Quartz | 666 | 14.0 | 8.9 | 0 | 0 | 29.8 | 0 | 43.9 | 17.4 |
| n-C$_3$H$_8$ | C | 662 | 52.8 | 9.9 | 32.8 | 2.0 | 42.8 | 0 | 4.6 | 7.4 |
| n-C$_3$H$_8$ | C | 664 | 48.7 | 10.3 | 33.6 | 2.3 | 44.5 | 0 | 4.5 | 4.8 |
| n-C$_3$H$_8$ | Quartz | 672 | 26.0 | 10.3 | 29.6 | 1.1 | 43.9 | 0 | 0 | 12.9 |
| C$_2$H$_6$ | C | 668 | 44.8 | 0 | 95.8 | 0 | 0.5 | 0 | 0 | 3.7 |

*The runs over catalyst C are all over the same sample in the sequence shown.
The runs over quartz are all over the same sample in the same sequence and time as for catalyst C.

Reasonable variations and modifications are possible within the scope of the disclosure and the appended claims to the invention.

about 180° C. for at least 5 hours and wherein said catalyst composition is calcined in a nitrogen atmosphere at a temperature in the range of about 450° C. to about 850° C. for a time in the range of about 1 hour to about 12 hours.

10. A composition in accordance with claim 8 wherein said catalyst composition is dried in the presence of free oxygen at a temperature in the range of about 130° C. to about 150° C. for at least 5 hours and wherein said catalyst composition is calcined in a nitrogen atmosphere at a temperature in the range of about 700° C. to about 800° C. for a time in the range of about 2 hours to about 5 hours.

11. A composition in accordance with claim 7 wherein said catalyst composition additionally comprises at least one halogen selected from the group consisting of chlorine, bromine and iodine.

12. A composition in accordance with claim 1 wherein said catalyst composition additionally comprises at least one halogen selected from the group consisting of chlorine, bromine and iodine.

* * * * *